US012765977B2

(12) United States Patent
Kim

(10) Patent No.: US 12,765,977 B2
(45) Date of Patent: Oct. 20, 2026

(54) METHOD AND DEVICE FOR PROVIDING EXPECTED ERROR INFORMATION RELATED TO IMPLANT PLACEMENT

(71) Applicant: OSSTEM IMPLANT CO., LTD., Seoul (KR)

(72) Inventor: Jong Moon Kim, Gunpo-si (KR)

(73) Assignee: OSSTEM IMPLANT CO., LTD., Seoul (KR)

(*) Notice: Subject to any disclaimer, the term of this patent is extended or adjusted under 35 U.S.C. 154(b) by 160 days.

(21) Appl. No.: 18/868,729

(22) PCT Filed: Apr. 27, 2023

(86) PCT No.: PCT/KR2023/005771

§ 371 (c)(1),
(2) Date: Nov. 22, 2024

(87) PCT Pub. No.: WO2024/025087

PCT Pub. Date: Feb. 1, 2024

(65) Prior Publication Data

US 2025/0169928 A1 May 29, 2025

(30) Foreign Application Priority Data

Jul. 26, 2022 (KR) ........................ 10-2022-0092686

(51) Int. Cl.
*A61C 13/00* (2006.01)
*A61B 1/00* (2006.01)
(Continued)

(52) U.S. Cl.
CPC ...... *A61C 13/0004* (2013.01); *A61B 1/00009* (2013.01); *A61B 1/24* (2013.01);
(Continued)

(58) Field of Classification Search
CPC .................. A61B 1/00009; A61B 1/24; A61B 2090/3937; A61B 34/10; A61B 5/00;
(Continued)

(56) References Cited

U.S. PATENT DOCUMENTS 5,967,777 A * 10/1999 Klein .................. A61C 9/0053 433/76
8,932,058 B2 1/2015 Fisker et al.
(Continued)

FOREIGN PATENT DOCUMENTS

JP 2009-517144 A 4/2009
KR 10-1375065 B1 3/2014
(Continued)

OTHER PUBLICATIONS

Korean Intellectual Property Office, International Search Report, International Application No. PCT/KR2023/005771, Aug. 17, 2023.

*Primary Examiner* — Michael J Vanchy, Jr.
(74) *Attorney, Agent, or Firm* — NSIP Law

(57) ABSTRACT

A method includes obtaining first intraoral data on the basis of imaging or scanning an oral cavity, obtaining a guide wearing simulation model for simulating a state in which a guide template model obtained on the basis of the first intraoral data is applied to the intraoral data, obtaining second intraoral data on the basis of imaging or scanning performed while a guide template corresponding to the guide template model is worn on the oral cavity, obtaining a fiducial marker wearing scan model indicating a state in which the guide template is worn on the oral cavity on the basis of the second intraoral data, and providing expected error information regarding a position of an implant model using a first fiducial marker model in which a fiducial marker
(Continued)

is coupled to the guide wearing simulation model and a second fiducial marker model corresponding to the fiducial marker wearing scan model.

20 Claims, 17 Drawing Sheets

(51) Int. Cl.

| | |
|---|---|
| ***A61B 1/24*** | (2006.01) |
| ***A61B 90/00*** | (2016.01) |
| ***A61C 1/08*** | (2006.01) |
| ***G06T 7/73*** | (2017.01) |

(52) U.S. Cl.
CPC ................ *A61C 1/084* (2013.01); *G06T 7/75* (2017.01); *A61B 2090/3937* (2016.02); *G06T 2207/30036* (2013.01); *G06T 2207/30204* (2013.01)

(58) Field of Classification Search
CPC ....... A61C 1/08; A61C 1/084; A61C 13/0004; A61C 8/00; A61C 9/00; A61C 9/0053; G06T 1/00; G06T 17/00; G06T 19/20; G06T 2207/30036; G06T 2207/30204; G06T 7/00; G06T 7/75; G16H 30/00; G16H 50/50
See application file for complete search history.

(56) References Cited

U.S. PATENT DOCUMENTS

| | | | |
|---|---|---|---|
| 12,011,230 | B2 | 6/2024 | Wang |
| 2009/0220916 | A1 | 9/2009 | Fisker et al. |
| 2015/0073577 | A1 | 3/2015 | Fisker et al. |
| 2022/0054200 | A1 | 2/2022 | Wang |

FOREIGN PATENT DOCUMENTS

| | | | |
|---|---|---|---|
| KR | 10-1797155 | B1 | 11/2017 |
| KR | 10-2020-0072250 | A | 6/2020 |
| KR | 10-2021-0027623 | A | 3/2021 |
| KR | 10-2021-0084556 | A | 7/2021 |
| KR | 10-2021-0127280 | A | 10/2021 |
| KR | 10-2021-0136573 | A | 11/2021 |
| KR | 10-2021-0142357 | A | 11/2021 |
| KR | 10-2021-0150633 | A | 12/2021 |
| KR | 10-2363412 | B1 | 2/2022 |

* cited by examiner (a)

(b)

(a)

(b)

(a)

(b)

METHOD AND DEVICE FOR PROVIDING EXPECTED ERROR INFORMATION RELATED TO IMPLANT PLACEMENT

CROSS-REFERENCE TO RELATED APPLICATIONS

This application is a National Stage of International patent application PCT/KR2023/005771, filed on Apr. 27, 2023, which claims priority of foreign Korean patent application No. KR 10-2022-0092686, filed on Jul. 26, 2022, the disclosures of which are hereby incorporated by reference in their entireties.

TECHNICAL FIELD

The present disclosure relates to a device and method for providing expected error information related to implant replacement. A guide template is used to ensure accurate implant placement. The present disclosure relates to a technique for improving the accuracy of the guide template prior to implant placement.

BACKGROUND ART

In conventional dental implant surgery, a method of establishing an implant surgery plan using software prior to surgery has been used.

The process of establishing a dental implant surgery plan with software generally involves acquiring the patient's CT data and scan data, aligning them, and, based on the patient's anatomical structure, developing a surgical plan to determine the positions of implant structures (e.g., implant, abutment, crown, anchor pin, etc.), followed by designing the shape of a surgical guide according to the plan information. Afterward, the guide is printed using a 3D printer. At this time, it is important to identify errors in the process of designing and printing the surgical guide using the software, as well as any errors that may arise from incorrectly fastening the surgical guide during the surgery, before the surgery itself. Otherwise, the implant may be placed in a position different from the planned one. Thus, the accuracy of the surgical guide implant placement position before the implant is placed is crucial. Accordingly, there is a need for a technique that provides a concrete method to provide expected error information to ensure accurate implant placement positioning before the implant is placed.

DISCLOSURE

Technical Problem

An embodiment of the present disclosure aims to address the problems of the prior art described above, specifically, the issue that the implant placement position determined by the conventional surgical guide may not be accurate, and an object of the present disclosure is to provide an accurate implant placement position for each patient's oral cavity before implant placement. Also, an embodiment of the present disclosure aims to address the aforementioned problems of the prior art by providing error information regarding a three-dimensional virtual implant placement position before surgery. The technical objectives to be addressed are not limited to those mentioned above, and various other objectives may be further included within the scope obvious to those of ordinary skill in the art.

Technical Solution

According to a first aspect of the present disclosure, a method performed by a device for providing expected error information related to implant placement may include the steps of: obtaining first intraoral data on the basis of imaging or scanning an oral cavity; obtaining a guide wearing simulation model for simulating a state in which a guide template model obtained on the basis of the first intraoral data is applied to the intraoral data; obtaining second intraoral data on the basis of imaging or scanning performed while a guide template corresponding to the guide template model is worn on the oral cavity; obtaining a fiducial marker wearing scan model indicating a state in which the guide template is worn on the oral cavity on the basis of the second intraoral data; and providing expected error information regarding a position of an implant model by using a first fiducial marker model in which a fiducial marker is coupled to the guide wearing simulation model and a second fiducial marker model corresponding to the fiducial marker wearing scan model.

The guide template may be produced based on the guide template model and may be used to couple one or more fiducial markers.

The step of providing the expected error information may include a step of obtaining the expected error information based on a comparison result between a first expected position of the implant model, determined by a position of the first fiducial marker model, and a second expected position of the implant model, determined by a position of the second fiducial marker model.

The step of providing the expected error information may include the steps of: determining the first expected position based on a first axial direction oriented by the first fiducial marker model and positions of a plurality of first reference points on the first fiducial marker; determining the second expected position based on a second axial direction oriented by the second fiducial marker model and positions of a plurality of second reference points on the second fiducial marker; and obtaining the expected error information based on the comparison result between the first expected position and the second expected position.

The step of providing the expected error information may include the steps of: obtaining a first gingival reference point for the guide wearing simulation model; obtaining a second gingival reference point for the fiducial marker wearing scan model; obtaining an intraoral matching model in which the guide wearing simulation model and the fiducial marker wearing scan model are matched with respect to the first gingival reference point and the second gingival reference point corresponding to the first gingival reference point; and superimposing, based on the intraoral matching model, and displaying an implant model of the first expected position and an implant model of the second expected position.

The step of providing the expected error information may include the steps of: automatically or based on user input obtaining a first gingival reference point for the guide wearing simulation model; obtaining relative position information indicating a relative position relationship between the first gingival reference point and the first fiducial marker model; obtaining, based on the relative position information, the second gingival reference point, corresponding to the first gingival reference point, on the fiducial marker wearing scan model; obtaining an intraoral matching model in which the guide wearing simulation model and the fiducial marker wearing scan model are matched by aligning the first gingival reference point and the second gingival reference point; and obtaining the expected error information on the basis of the intraoral matching model.

A position of the automatically obtained gingival reference point may be generated on an area of the entire guide wearing simulation model excluding the guide template model or on an area of the entire fiducial marker wearing scan model excluding the guide template, and the user input may be applied to the area of the entire guide wearing simulation model excluding the guide template model or to the area of the entire fiducial marker wearing scan model excluding the guide template model.

The relative position information may include distance information between a plurality of first reference points on the first fiducial marker model and the first gingival reference point or distance information between a plurality of second reference points on the second fiducial marker model and the second gingival reference point.

The step of obtaining the intraoral matching model may include obtaining the intraoral matching model by updating a viewpoint of the first intraoral data or a viewpoint of the second intraoral data in a state where the first gingival reference point and the second gingival reference point are aligned.

According to a second aspect of the present disclosure, a device for providing expected error information related to implant placement may include a processor configured to: obtain first intraoral data on the basis of imaging or scanning an oral cavity; obtain a guide wearing simulation model for simulating a state in which a guide template model obtained on the basis of the first intraoral data is applied to the intraoral data; obtain second intraoral data on the basis of imaging or scanning performed while a guide template corresponding to the guide template model is worn on the oral cavity; obtain a fiducial marker wearing scan model indicating a state in which the guide template is worn on the oral cavity on the basis of the second intraoral data; and provide expected error information regarding a position of an implant model by using a first fiducial marker model coupled to the guide wearing simulation model and a second fiducial marker model coupled to the fiducial marker wearing scan model.

The guide template may be produced based on the guide template model and may be used to couple one or more fiducial markers.

The processor may obtain the expected error information based on a comparison result between a first expected position of the implant model, determined by a position of the first fiducial marker model, and a second expected position of the implant model, determined by a position of the second fiducial marker model.

The processor may determine the first expected position based on a first axial direction oriented by the first fiducial marker model and positions of a plurality of first reference points on the first fiducial marker, determine the second expected position based on a second axial direction oriented by the second fiducial marker model and positions of a plurality of second reference points on the first fiducial marker, and obtain the expected error information based on the comparison result between the first expected position and the second expected position.

The processor may obtain a first gingival reference point for the guide wearing simulation model automatically or based on user input, obtain relative position information indicating a relative position relationship between the first gingival reference point and the first fiducial marker model, obtain, based on the relative position information, the second gingival reference point, corresponding to the first gingival reference point, on the fiducial marker wearing scan model, obtain an intraoral matching model in which the guide wearing simulation model and the fiducial marker wearing scan model are matched by aligning the first gingival reference point and the second gingival reference point, and obtain the expected error information on the basis of the intraoral matching model.

According to a third aspect of the present disclosure, there may be provided a computer-readable, non-transitory recording medium having stored thereon a program which, when executed by a computer system, causes the computer system to implement the method of the first aspect.

Advantageous Effects

According to an embodiment of the present disclosure, the method or device in accordance with the present disclosure is efficient in determining an anticipated three-dimensional virtual implant position based on specific shapes and locations of fiducial markers, as the implant placement position is determined using fiducial markers.

Additionally, the method or device according to the present disclosure improves efficiency by providing anticipated surgical error information by comparing a three-dimensional virtual implant position planned for surgery using a fiducial marker and the position of a three-dimensional virtual implant based on the position of a guide coupled in the patient's oral cavity. This allows a user to utilize the information to adjust the coupling of the guide or to redesign the guide.

Moreover, since the method or device according to the present disclosure provides anticipated error information regarding the implant placement position to a user's account, allowing a guide to be adjusted or produced according to the information, it may help determine the implant placement position more suitable for the patient's oral cavity, thereby improving both user and patient satisfaction.

Furthermore, because the oral cavity is scanned using an intraoral scanner rather than by having the fiducial marker attached and performing a CT scan, there is no additional radiation exposure.

Effects according to the embodiments of the present disclosure are not limited to the above-described effects, and other effects not described will be clearly understood by those skilled in the art from the following description.

MODE OF THE INVENTION

While the terms used herein are selected from those that are currently most widely as possible in consideration of the functions in the present disclosure, these are subject to change depending on intents of those skilled in the art, precedents, or introduction of new technologies, etc. Further, in certain circumstances, some terms may be arbitrarily chosen by the Applicant, in which case the corresponding meaning will be defined in detail in the corresponding part of the description. Accordingly, the terms used herein should be defined based on the meanings thereof and the overall content of the disclosure, rather than simply based on what these terms are called.

Throughout the specification, it will be understood that when a component "includes (or comprises)" an element, unless there is another opposite description thereto, it should be understood that the component does not exclude another element but may further include another element. Furthermore, the term "unit (or part)" used in the specification refers to a unit for processing at least one function or operation, and this may be realized in the form of hardware, software, or in a combination of both hardware and software.

Embodiments of the present invention will now be described in detail with reference to the accompanying drawings so that those skilled in the art can easily practice the embodiments of the present disclosure. However, the present disclosure may be implemented in many different forms and is not limited to the embodiments described herein.

Hereinafter, embodiments of the present disclosure will be described in detail with reference to the drawings.

Figure 1:
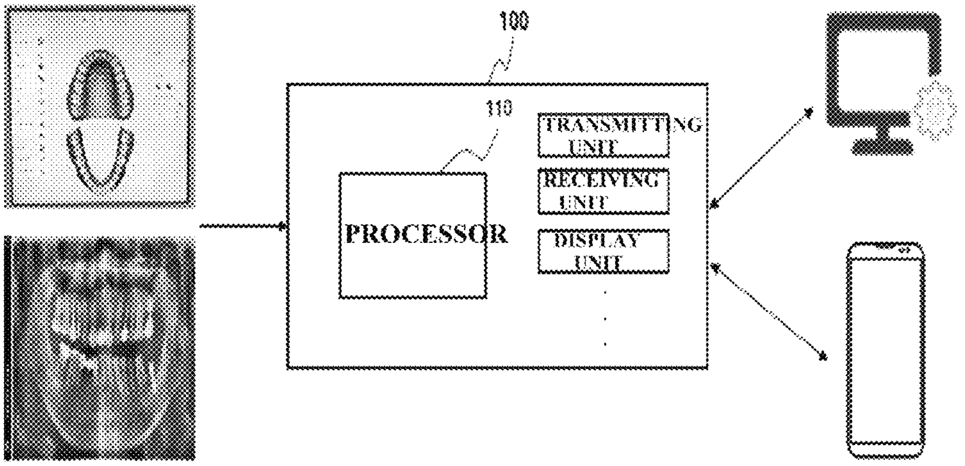
FIG. 1 is a block diagram illustrating an example of a configuration of a device according to an embodiment.

FIG. 1 is a block diagram illustrating an example of a configuration of a device 100 according to an embodiment.

Referring to FIG. 1, the device 100 may include a processor 110, a transmitting unit, a receiving unit, a display, and the like.

The processor 110 may obtain first intraoral data on the basis of imaging or scanning an oral cavity. In one embodiment, the intraoral data may refer to CT data, scan data, or the like related to the oral cavity. In addition, the processor 110 may obtain a guide wearing simulation model that simulates a state of a guide template model, obtained on the basis of the obtained first intraoral data, when worn in the oral cavity. In one embodiment, the term "model" may refer to virtual data rather than a physical object. For example, the guide template model is obtained for patient customization based on the patient's first intraoral data, and may refer to three-dimensional (3D) model data used to determine a guide template corresponding to the guide template model. Accordingly, the processor 110 may use the guide template model to simulate the state of the guide template when worn in the oral cavity through 3D modeling or similar methods. Moreover, the processor 110 may obtain second intraoral data on the basis of imaging or scanning conducted while the guide template, corresponding to the guide template model, is worn in the oral cavity. In one embodiment, the guide template may refer to the actual physical object corresponding to the guide template model. For example, the guide template may be output using the guide template model. Accordingly, the processor 110 may obtain CT data, scan data, or the like for the oral cavity with the obtained guide template worn as the second intraoral data. Additionally, the processor 110 may obtain a fiducial marker wearing scan model indicating the state in which the guide template is worn in the oral cavity, on the basis of the second intraoral data. For example, the first intraoral data may refer to data obtained through imaging or scanning of the oral cavity, while the second intraoral data refers to data obtained through scanning with the guide template worn on the oral cavity. Moreover, the guide wearing simulation model may include a 3D model that simulates the state of the guide template model, which is virtual data, when worn in the oral cavity, while the fiducial marker wearing scan model may include a 3D model representing the state of the actual guide template worn in the oral cavity.

In one embodiment, a fiducial marker may refer to a component that can be attached to the guide template as an element to confirm the fit for an expected implant placement position within the oral cavity. For example, to confirm the fit of the guide template for the expected implant placement position, one or more fiducial markers may be attached to the guide template model as a virtual model or attached to the guide template as a physical marker. The fiducial marker described herein may include both a virtual model marker and a physical marker attached to the actual guide template.

In one embodiment, the guide wearing simulation model is a model obtained by simulating the state in which the guide template model is applied to the intraoral data on the basis of the intraoral data acquired through imaging or scanning of the oral cavity, and the fiducial marker wearing scan model is obtained by imaging or scanning of the oral cavity after the guide template and fiducial marker are applied to the oral cavity.

The processor 110 may provide expected error information regarding a position of an implant model by using a first fiducial marker model, in which a fiducial marker is attached to the guide wearing simulation model, and a second fiducial marker model that corresponds to the fiducial marker wearing scan model. Since the fiducial marker wearing scan model is a 3D model acquired by performing scanning while the fiducial marker is attached to the guide template worn in the oral cavity, it may be difficult to view the entire shape of the fiducial marker. The second fiducial marker model may refer to a model that includes the shapes of fiducial markers that are not illustrated in the fiducial marker wearing scan model. However, the processor 110 may align the fiducial marker, as a virtual model, with the second fiducial marker model so that the entire shape of the fiducial marker is displayed in the fiducial marker wearing scan model.

For example, the processor 110 may provide a user terminal with expected error information regarding the position of the implant model, obtained using the first and second fiducial marker models. Any operation in which the device 100 receives information from or provides information to the user terminal may be performed through communication between the device 100 and the user terminal. Furthermore, to provide expected error information, the processor 110 may compare the position of the implant model using the first and second fiducial marker models. A detailed description of this process will be provided below by way of an embodiment.

In addition, it is understood by those skilled in the art that other general-purpose components, in addition to those shown in FIG. 1, may also be included in the device 100. According to one embodiment, the device 100 may further include an algorithm for processing CT image data or 2D/3D image data, an algorithm for automatically acquiring reference points on the gums, a user interface unit configured to receive user inputs, a storage unit configured to store data described throughout the specification, a receiving unit configured to receive data, and a transmitting unit configured to transmit data. For example, the receiving unit may include a wired and/or wireless communication device capable of transmitting and receiving various types of information by connecting to other devices or components through a network or signal processing module. In one embodiment, the processor 110 may perform a series of operations to acquire an oral model and a fiducial marker model based on the guide template model and guide template and to obtain expected error information regarding the implant position. The processor 110 may be electrically connected to the storage unit, the receiving unit, the transmitting unit, and other components to control data flow among them. To this end, the processor 110 may be implemented as a central processing unit (CPU) that controls the overall operation of the device 100. Various embodiments of the method performed by the device 100, according to one embodiment, for providing expected error information related to implant placement will be described in more detail below with reference to FIGS. 2 through 16.

Figure 2:
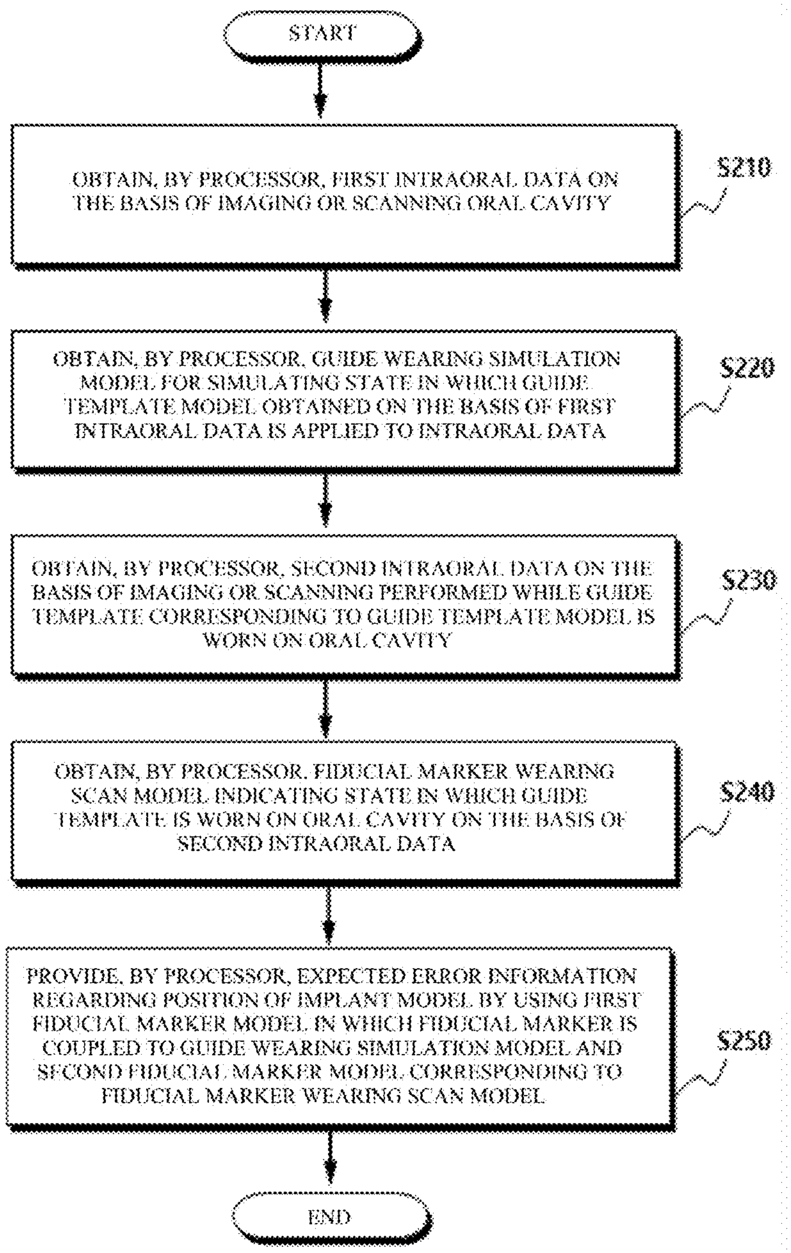
FIG. 2 is a flowchart illustrating a method performed by a device for providing expected error information related to implant placement, according to an embodiment.

FIG. 2 is a flowchart illustrating a method performed by the device 100, according to one embodiment, for providing expected error information related to implant placement.

Referring to FIG. 2, in step S210, the device 100 may obtain first intraoral data on the basis of imaging or scanning an oral cavity. In one embodiment, the device 100 may acquire information from imaging or scanning of the oral cavity, and based on this, obtain first intraoral data, including CT data, scan data, or the like for the oral cavity.

Additionally, the processor 110 may utilize data on a guide template model 300. For example, the processor 110 may perform simulations using the guide template model 300. The guide template model 300 may be understood with reference to FIG. 3, and a specific embodiment of the simulation may refer to step S220.

Figure 3:
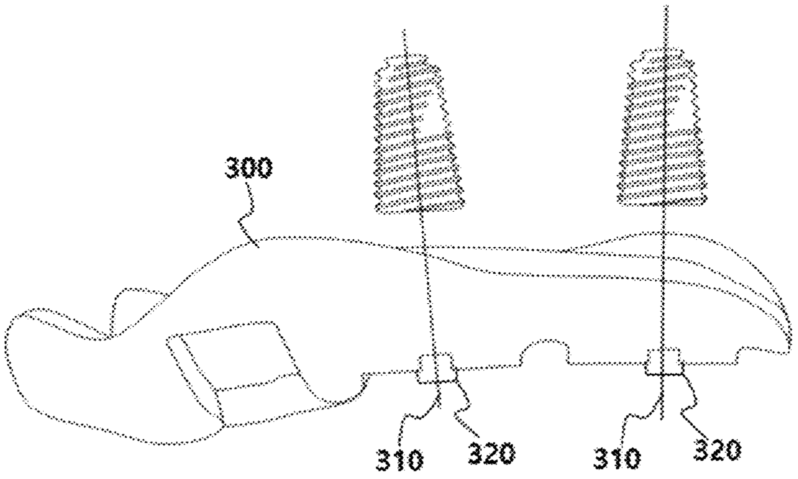
FIG. 3 illustrates a guide template model and an implant position according to an embodiment.

FIG. 3 illustrates the relative positions of the guide template model 300 and implants to be placed, according to one embodiment. As shown in FIG. 3, an implant may be placed along an implant axis 310 positioned at each drill hole 320 on the obtained guide template model 300. Hereinafter, the description is based on two implants to be placed, as shown in FIG. 3, but it is not necessarily limited thereto. The same can apply when one or more than three implants are placed.

In step S220, the device 100 may obtain a guide wearing simulation model that simulates the state in which the guide template model 300, obtained based on the first intraoral data, is applied to the intraoral data. In one embodiment, the guide template model 300 may refer to virtual data and may be implemented via 3D modeling or similar methods. For example, step S220 may be explained with reference to FIG. 5.

Figure 5:
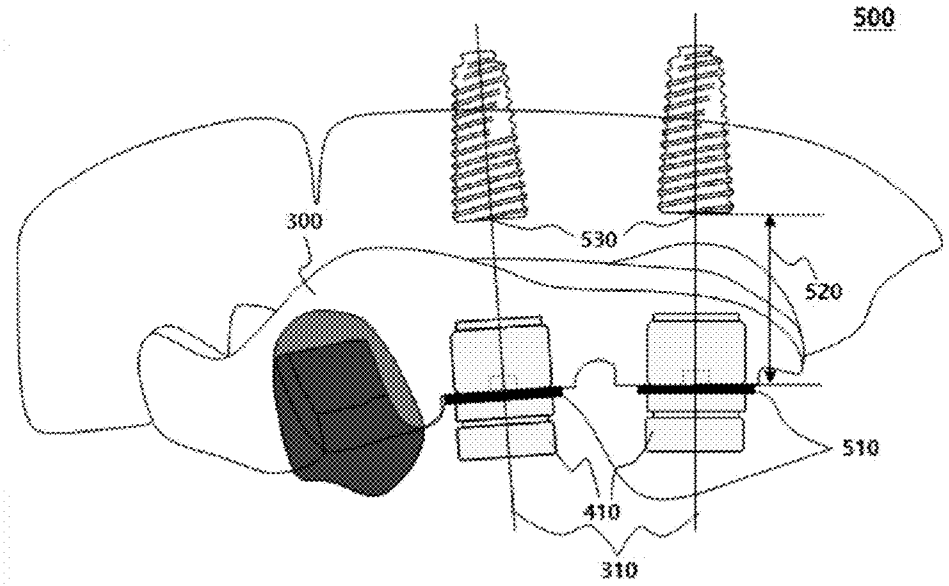
FIG. 5 illustrates an example in which a device, according to an embodiment, provides information on an implant position, which is determined on a basis of on a fiducial marker coupled to a guide template model, using a guide wearing simulation model.

FIG. 5 illustrates an example in which the device 100, according to an embodiment, provides information on the implant position, which is determined on the basis of fiducial markers 410 coupled to the guide template model 300, using a guide wearing simulation model 500.

In one embodiment, the guide template model 300 and the guide wearing simulation model 500 may include 3D model data, as shown in FIG. 5. The device 100 may obtain a guide template model 300 designed to fit based on tooth position information included in the first intraoral data and gum position information where the implant is required. Accordingly, the device 100 may further obtain a guide wearing simulation model 500 that indicates the state in which the obtained guide template model 300 is worn in the oral cavity.

In step S230, the device 100 may obtain second intraoral data on the basis of imaging or scanning performed while a guide template, corresponding to the guide template model 300, is worn in the oral cavity. In one embodiment, the guide template may refer to a physical object corresponding to the virtual guide template model 300. The device 100 may acquire information based on imaging or scanning of the oral cavity with the guide template in place and, based on this, obtain second intraoral data that includes CT data, scan data, and the like for the oral cavity with the guide template worn.

In one embodiment, the guide template may be produced based on the guide template model 300 and may be used to couple one or more fiducial markers 410. For example, the device 100 may first acquire the guide template model 300 as virtual data on the basis of the initially obtained first intraoral data to produce a physical guide template for the oral cavity. Consequently, the device 100 may obtain a physical guide template generated with the same shape as the acquired guide template model 300 by using a 3D printer or milling machine and it may acquire imaging or scan information for the oral cavity with the guide template worn as the second intraoral data.

For example, the processor 110 may obtain the guide template using the guide template model 300. The processor 110 may perform a simulation while the guide template is worn in the patient's oral cavity.

In addition, the processor 110 may perform a scan of the patient's oral cavity while the guide template is worn. This process may be described with reference to FIG. 4.

Figure 4:
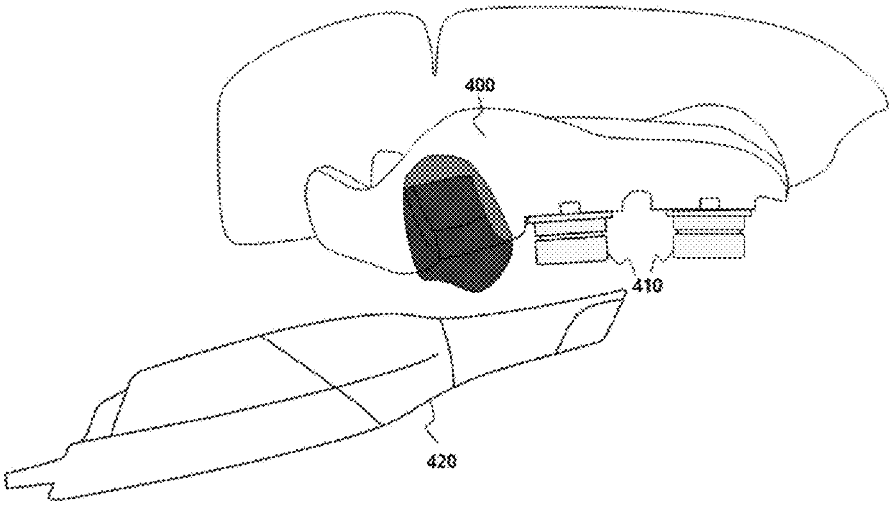
FIG. 4 illustrates an example of performing an intraoral scan with a guide template and fiducial marker coupled in a patient's oral cavity according to an embodiment.

FIG. 4 illustrates an example of performing an intraoral scan with the guide template 400 and fiducial marker 410 coupled in the patient's oral cavity according to an embodiment. Referring to FIG. 4, in one embodiment, an intraoral scanner 420 may be used to image or scan the oral cavity in which the guide template 400 to which the fiducial marker 410 is coupled is worn, and the device 100 may obtain information based on this imaging or scanning.

In one embodiment, to confirm the fit for an implant placement position in the oral cavity, one or more fiducial markers 410 may be coupled to the guide template 400. The device 100 may confirm the fit for the implant placement position in the oral cavity by checking or comparing the positions of one or more fiducial markers 410 coupled to the guide template 400.

In step S240, the device 100 may obtain a fiducial marker wearing scan model that indicates the state in which the guide template 400 is worn in the oral cavity, on the basis of the second intraoral data. The device 100 may obtain an image representing the state of the guide template 400 being worn in the oral cavity as the fiducial marker wearing scan model. Step S240 may be described with reference to FIG. 6.

Figure 6:
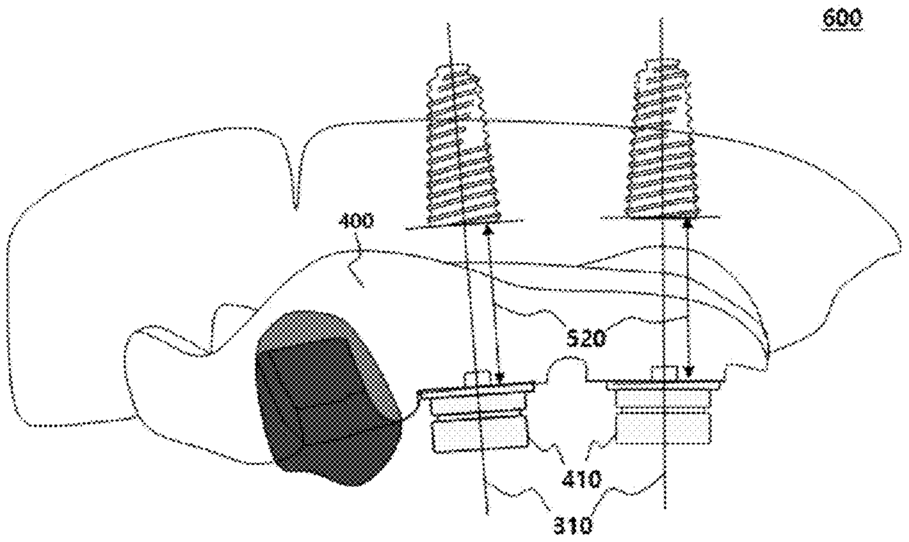
FIG. 6 illustrates an example in which a device, according to an embodiment, provides information on an implant position, which is determined on a basis of a fiducial marker coupled to a guide template, using a fiducial marker wearing scan model.

FIG. 6 illustrates an example in which the device 100, according to one embodiment, provides information on the implant position determined on the basis of the fiducial markers 410 coupled to the guide template 400, using a fiducial marker wearing scan model 600.

In one embodiment, the guide template 400 and the fiducial marker wearing scan model 600 may include actual patient intraoral scan data as a 3D model, as shown in FIG. 6. Accordingly, the device 100 may additionally obtain the fiducial marker wearing scan model 600 that indicates the state in which the obtained guide template 400 is worn in the oral cavity.

In step S250, the device 100 may provide expected error information regarding the position of the implant model by using a first fiducial marker model, in which the fiducial marker is coupled to the guide wearing simulation model 500, and the second fiducial marker model, which corresponds to the fiducial marker wearing scan model 600. Step S250 may be described with reference to FIG. 7.

Figure 7:
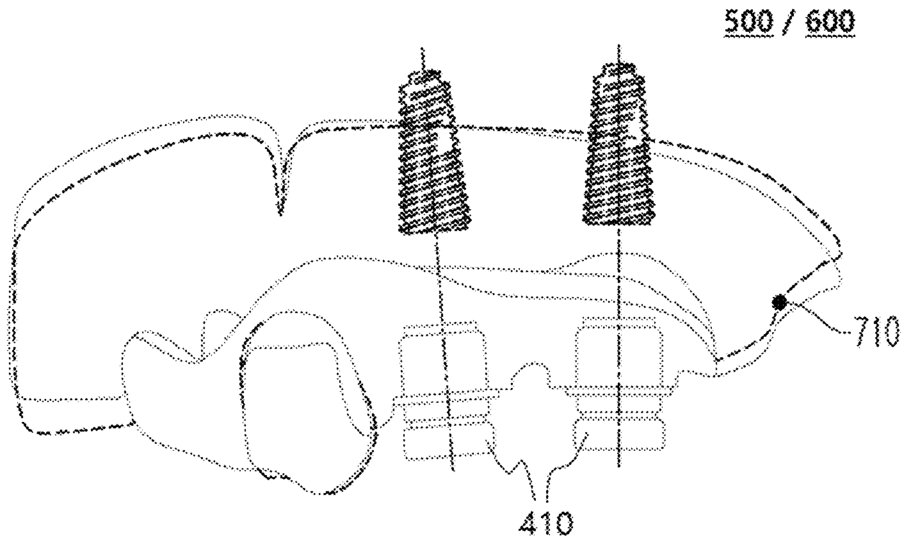
FIG. 7 illustrates a case where a device, according to an embodiment, aligns a guide wearing simulation model and a fiducial marker wearing scan model, based on a fiducial marker model.

FIG. 7 illustrates an alignment of the guide wearing simulation model 500 and the fiducial marker wearing scan model 600 based on a fiducial marker model. In FIG. 7, the guide wearing simulation model 500 is shown in dotted lines, while the fiducial marker wearing scan model 600 is shown in solid lines.

When aligning a first fiducial marker model coupled to the guide wearing simulation model 500 and a second fiducial marker model coupled to the fiducial marker wearing scan model 600 and comparing each fiducial marker 410 and implant position contained in the two fiducial marker models, it may not be possible to accurately obtain the expected error of the implant model. This is because the expected position of the implant model is determined based on the position of the fiducial marker model. When alignment is performed based on the positions of the first fiducial marker model and the second fiducial marker model, a first expected position of the implant, determined by the first fiducial marker model, and a second expected position of the implant, determined by the second fiducial marker model, may become identical.

For example, the first and second fiducial markers may be essential elements for the device 100 to obtain the expected error information regarding the position of the implant model. As described with reference to FIG. 7, when the first fiducial marker model and the second fiducial marker model are aligned based on the positions of each of the first and second fiducial markers included in the two fiducial marker models, the first and second expected positions of the implant may become identical. Therefore, the device 100 may obtain a separate gingival reference point 710. The device 100 may obtain expected error information regarding the first and second expected positions of the implant using the obtained gingival reference point 710. The method of obtaining expected error information for the implant model using the gingival reference point 710 will be described below.

In one embodiment, the device 100 may obtain expected error information based on a comparison result between the first expected position of the implant model, determined by the position of the first fiducial marker model, and the second expected position of the implant model, determined by the position of the second fiducial marker model. The device 100 may obtain the expected error information by comparing the first expected position and the second expected position, which are determined based on the positional relationship among the gingival reference point 710, at least one point within the first fiducial marker, and at least one point within the second fiducial marker.

For example, the device 100 may determine the first expected position based on a first axial direction oriented by the first fiducial marker model and the position of at least one point within the first fiducial marker, and determine the second expected position based on a second axial direction oriented by the second fiducial marker model and the position of at least one reference point within the second fiducial marker. In one embodiment, the first axial direction may correspond to the direction in which the implant axis 310 within the first fiducial marker model is oriented, and the second axial direction may correspond to the direction in which the implant axis 310 within the second fiducial marker is oriented. Thus, the first expected position for the implant model may be determined at a position along the first axial direction, and the second expected position may be determined at a position along the second axial direction. In one embodiment, at least one reference point within first CT data and a reference point within second CT data may be included in each fiducial marker 410 in each fiducial marker model. Step S250 may be described with reference to FIG. 8.

Figure 8:
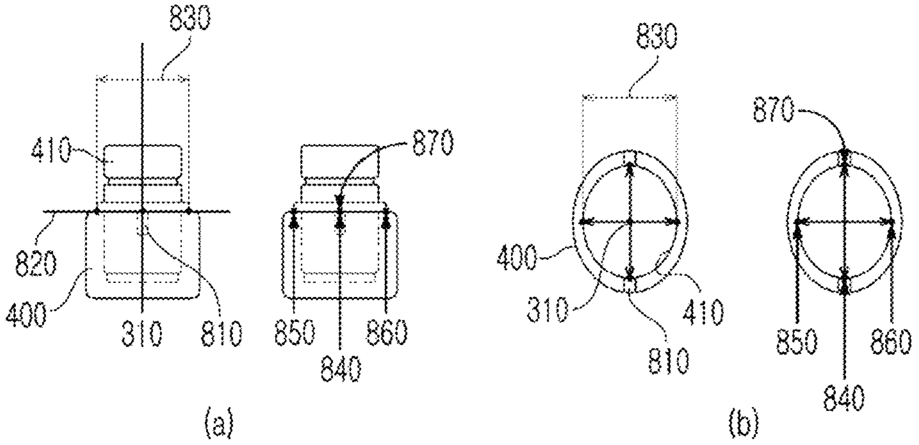
FIG. 8 illustrates an example of a method of determining at least one reference point within a fiducial marker, according to an embodiment.

FIG. 8 illustrates an example of a method of determining at least one reference point within the fiducial marker 410 according to an embodiment. Additionally, FIG. 8 is presented in correspondence with the guide template 400 shown in FIG. 9 and illustrates the relationship between the guide template 400 and the fiducial marker 410 by isolating the fiducial marker 410 for one guide hole.

(a) in FIG. 8 is a side view showing a state in which the fiducial marker 410 is coupled to the guide template 400, and (b) in FIG. 8 is a bottom view showing a state in which the fiducial marker 410 is coupled to the guide template 400. In one embodiment, referring to (a) of FIG. 8, the device 100 may automatically obtain a fiducial marker plane 820 indicating a fastening point between the guide template 400 and the fiducial marker

410. The device 100 may determine the expected implant position using the fiducial marker plane 820.

Additionally, referring to FIG. 8, the device 100 may identify and determine the positions of a plurality of reference points within the fiducial marker 410 by using a hex recess 810 of the guide template 400 to which the fiducial marker 410 is coupled. The device 100 may determine the expected implant position using the plurality of reference points within the fiducial marker 410, including a first reference point 840, a second reference point 850, a third reference point 860, and a fourth reference point 870. For example, the device 100 may determine four points as the plurality of reference points, positioned every 90 degrees from a point on a straight line aligned with the implant axis 310 and oriented toward the hex recess 810 of the guide template. The hex recess 810 of the guide template may refer to a groove designed to align with the implant's internal hexagon. In one embodiment, although the hex recess 810 is not specifically mentioned in FIGS. 4, 5, and 6, it is shown schematically. Therefore, the plurality of reference points may include each end point of a fiducial marker diameter 830, excluding the hex recess 810 of the guide template. In one embodiment, the device 100 may determine four reference points by setting a plurality of reference points corresponding to positions at 90-degree intervals on the fiducial marker plane 820 relative to the implant axis 310 and the hex recess 810 of the guide template, as shown in (b) of FIG. 8. Thus, each reference point may be positioned 90 degrees apart from each other, as illustrated in (b) of FIG. 8. For example, the fourth reference point 870 may be positioned 180 degrees from the first reference point 840, and the third reference point 860 may be positioned 180 degrees from the second reference point 850. Accordingly, the device 100 may determine a plane corresponding to the determined plurality of reference points. In one embodiment, the plane that corresponds to the plurality of reference points may be the fiducial marker plane 820. The device 100 may use the fiducial marker plane 820 to determine the first expected position and the second expected position for the implant. The device 100 may determine the position located at a preset distance 520 along the implant axis 310 from the fiducial marker plane 820 on which the fiducial marker 410 is coupled to the guide template 400 to be the uppermost position 530 of the implant.

Figure 9:
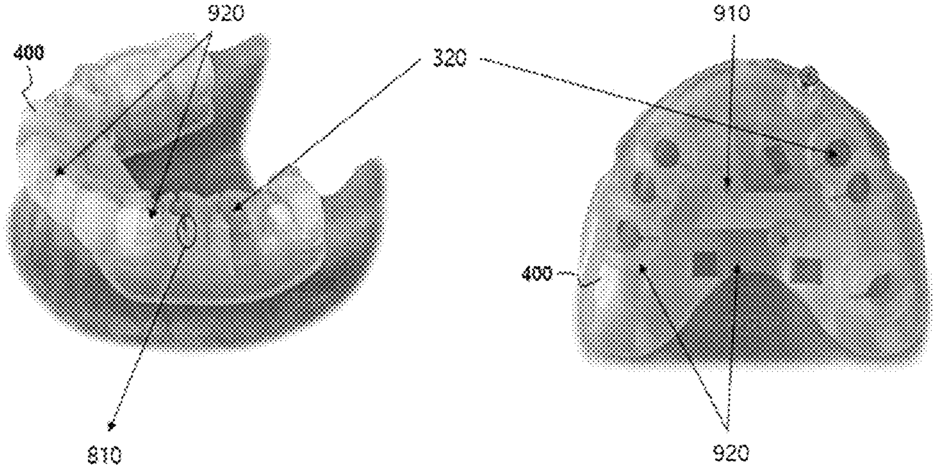
FIG. 9 illustrates an example showing a state in which the guide template, according to an embodiment, is worn in the patient's oral cavity.

FIG. 9 illustrates an example showing the state in which the guide template 400, according to an embodiment, is worn in the patient's oral cavity. As described with reference to FIG. 8, the guide template 400 may include the hex recess 810, a drill hole 320 for implant placement, an anchor screw hole 910 for securing the guide template 400, and an open window 920 for checking template fit.

In one embodiment, referring to FIGS. 5 and 6, as described with reference to FIG. 8, the device 100 may acquire the fiducial marker plane 820 contained in the widest part 510 of the fiducial marker. The device 100 may determine the point located at the predetermined distance 520 along the implant axis 310 from the fiducial marker plane 820 to be the implant uppermost position 530. In one embodiment, the implant axis 310 may be identical to the axis passing through the center of the fiducial marker 410. Thus, the device 100 may determine the expected position of the implant on the basis of the determined implant uppermost position 530. In one embodiment, the preset distance 520 may refer to a value representing a preset length for determining the implant placement position based on the position of the fiducial marker 410 and may, for example, be a value of 10.5 mm. In one embodiment, the preset distance 520 may be flexibly adjusted depending on the circumstances and may be preset or modified by an administrator or user. Using the method described with reference to FIGS. 5, 6, and 8, the device 100 may determine a first expected position and a second expected position for the implant positions corresponding to the first fiducial marker model and the second fiducial marker model.

In one embodiment, the device 100 may obtain a first gingival reference point for the guide wearing simulation model 500 and a second gingival reference point for the fiducial marker wearing scan model 600. In addition, the device 100 may obtain an intraoral matching model in which the guide wearing simulation model 500 and the fiducial marker wearing scan model 600 are matched with respect to the first gingival reference point and the second gingival reference point corresponding to the first gingival reference point. Based on the intraoral matching model, the device may superimpose and display the implant model of the first expected position and the implant model of the second expected position. In one embodiment, the first gingival reference point or the second gingival reference point may be determined by the device 100. For example, the device 100 may set a point within the guide wearing simulation model 500 as the first gingival reference point. The first gingival reference point may serve as a reference point for comparing each expected implant position determined in the guide wearing simulation model 500 and the fiducial marker wearing scan model 600. Since the first gingival reference point is the reference point for aligning and comparing the positions of the guide wearing simulation model 500 and the fiducial marker wearing scan model 600, the second gingival reference point corresponding to the first gingival reference point may represent the same position in terms of coordinates. Therefore, they may be commonly referred to as a gingival reference point 710. When the gingival reference point 710, including both the first and second gingival reference points, is located within the guide template model 300 or guide template 400, the guide wearing simulation model 500 and the fiducial marker wearing scan model 600 may be aligned at the same locations, and thus a comparison for each implant position may not be possible. Therefore, the gingival reference point 710 should not be positioned within the guide template model 300 or the guide template 400 but may be located on the gums. The device 100 may align the guide wearing simulation model 500 and the fiducial marker wearing scan model 600 with respect to the gingival reference point 710, and may obtain an intraoral matching model in which the guide wearing simulation model 500 and the fiducial marker wearing scan model 600 are matched. Accordingly, the device 100 may compare the positions of the implant model at the first expected position and the implant model at the second expected position on the basis of the intraoral matching model, in which the guide wearing simulation model 500 and the fiducial marker wearing scan model 600, which are aligned with respect to the gingival reference point 710, are matched. Additionally, the device 100 may display the superimposed image of the guide wearing simulation model 500 and the fiducial marker wearing scan model 600. In one embodiment, although the example is provided in which the device 100 determines the first gingival reference point, where a point in the fiducial marker-wear scan model 600 corresponding to the first gingival reference point is determined to be the second gingival reference point, then aligns the guide wearing simulation model 500 and the fiducial marker wearing scan model 600 with respect to the gingival reference point 710 to compare the positions of each implant model, the device

100 is not limited to this case. In another example, the device 100 may set a point within the fiducial marker wearing scan model 600 as the second gingival reference point, and a point within the guide wearing simulation model 500 corresponding to the second gingival reference point may be determined to be the first gingival reference point.

In another embodiment, the device 100 may automatically obtain the first gingival reference point for the guide wearing simulation model 500, or it may be obtained based on user input. The device 100 may obtain relative position information indicating the relative position between the first gingival reference point and the first fiducial marker model, and based on this relative position information, the device 100 may obtain the second gingival reference point, corresponding to the first gingival reference point, on the fiducial marker wearing scan model 600. Based on the distance between the first gingival reference point and the first fiducial marker model, the second gingival reference point may be obtained at the same distance from the second fiducial marker model, and the positions of the first and second gingival reference points may represent the same three-dimensional position in coordinates. Additionally, the device 100 may obtain an intraoral matching model in which the guide wearing simulation model 500 and the fiducial marker wearing scan model 600 are matched by aligning the first and second gingival reference points, and may obtain the expected error information on the basis of the intraoral matching model. The device 100 may automatically determine one point within the image of the guide wearing simulation model 500 or fiducial marker wearing scan model to be the position of the first or second gingival reference point, based on a preset algorithm. For example, the device 100 may obtain the first or second gingival reference point at a location beyond a preset distance away from the fiducial marker 410. Because the position of each fiducial marker 410 coupled to the guide template model 300 and the guide template 400 is specified, the device may determine a point beyond a preset distance away from the fiducial marker 410, based on the shapes of the guide template model 300 and the guide template 400 and the positions of each fiducial marker 410, to be the three-dimensional location of the first or second gingival reference point. This allows the first or second gingival reference point to be obtained at a position outside the guide template model 300 or the guide template 400. In addition, the device 100 may provide images of the guide wearing simulation model 500 and the fiducial marker wearing scan model 600 to the user terminal, and may receive a point within the image of the guide wearing simulation model 500 or the fiducial marker wearing scan model 600, which is input from a user, to be a first gingival reference point or a second gingival reference point. In one embodiment, the user input may be applied to an area of the entire guide wearing simulation model 500 excluding the guide template model 300. For example, the device 100 may provide the user terminal with a graphical UI that allows the user to select the location of the first gingival reference point on the gums within the guide template model 300. For example, the device 100 may provide the user terminal with a graphical UI that is set not to be clicked at a location within the image of the guide template model 300 or the guide template 400. Accordingly, the user may select one point within the area of the entire guide wearing simulation model 500 excluding the guide template model 300 or the guide template 400 to be the first gingival reference point or the second gingival reference point and may input the selected point. In one embodiment, the relative position information may include distance information between the plurality of first reference points on the first fiducial marker model and the first gingival reference point. For example, the device 100 may measure distances of each of the first reference point 840, the second reference point 850, the third reference point 860, and the fourth reference point 870, which are determined from the fiducial marker 410 within the guide wearing simulation model 500, from the first gingival reference point. In one embodiment, the distance information may include length, axial direction, etc.

Figure 10:
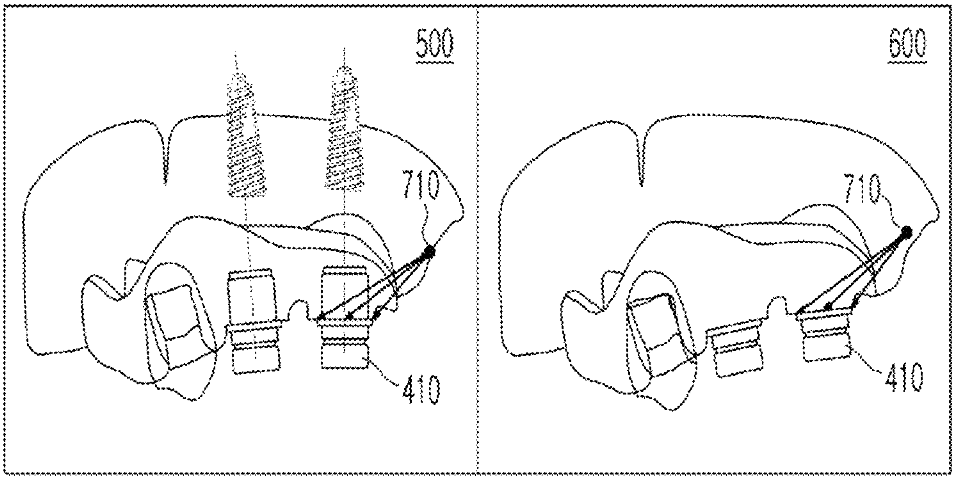
FIG. 10 illustrates an example of a method performed by a device, according to an embodiment, for determining a second gingival reference point by using a first gingival reference point and distance information of a fiducial marker.

FIG. 10 illustrates an example of a method performed by the device 100, according to an embodiment, for determining the second gingival reference point by using the first gingival reference point and the distance information of the fiducial marker 410.

Referring to the left illustration in FIG. 10, the device 100 may obtain distance information by measuring distances of the plurality of reference points within each fiducial marker 410 from the determined first gingival reference point along each axial direction (angle) in the guide wearing simulation model 500. In addition, referring to the right illustration in FIG. 10, showing an intraoral scan data image, the device 100 may determine a three-dimensional position of the second gingival reference point in the fiducial worn scan model 600 on the basis of the obtained distance information. For example, based on the distance (length) of the plurality of reference points within each fiducial marker 410 from the gingival reference point 710 along each axial direction (angle), included in the distance information obtained using the guide wearing simulation model 500, the three-dimensional position the same distance away from the plurality of reference points within each fiducial marker of the fiducial marker wearing scan model 600 may be determined to be the second gingival reference point. In one embodiment, the location of the first gingival reference point and the location of the second gingival reference point may be identical locations in coordinates, acting as reference points to be used for aligning the guide wearing simulation model 500 and the fiducial marker wearing scan model 600, when they are superimposed, and may refer to the gingival reference point 710. Therefore, the device 100 may obtain the relative position information between the first gingival reference point and the plurality of reference points within the fiducial marker 410 of the first fiducial marker model, and determine the position of the corresponding second gingival reference point within the fiducial marker wearing scan model 600. In addition, in one embodiment, the example has been described in which the device 100 determines the position of the second gingival reference point in the fiducial marker wearing scan model 600 by using the distance information between the first gingival reference point and the plurality of reference points of the fiducial marker 410 in the guide wearing simulation model 500, but is not limited thereto, and in another example, the device 100 may also determine the position of the first gingival reference point in the guide wearing simulation model 500 by using distance information between the second gingival reference point and a plurality of reference points of the fiducial marker 410 in the fiducial marker wearing scan model 600. In addition, the device 100 may display the guide wearing simulation model 500 and the fiducial marker wearing scan model 600 in a state in which the guide template model 300 and the guide template 400, which are aligned with the gingival reference point 710 based on the positions of the fiducial marker 410 and the gingival reference point 710, are worn in the oral cavity.

Figure 11:
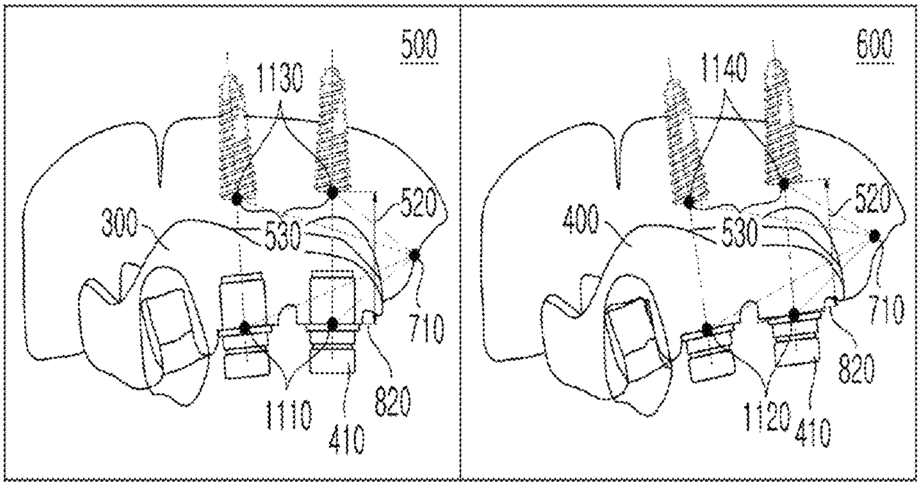
FIG. 11 illustrates an example of a method performed by the device, according to an embodiment, for obtaining a first figure and a second figure.

FIG. 11 illustrates an example of a method performed by the device 100 according to an embodiment for obtaining a first figure and a second figure.

Figure 12:
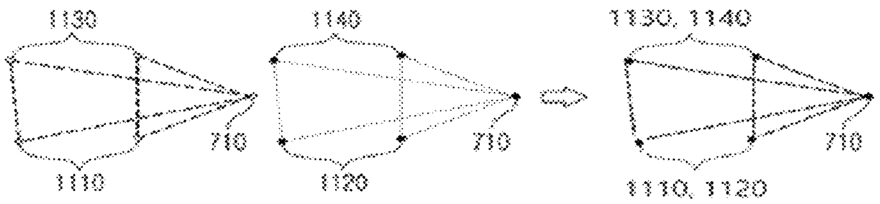
FIG. 12 illustrates an example of a case in which there is no fit error in an intraoral matching model according to an embodiment.
Figure 12:
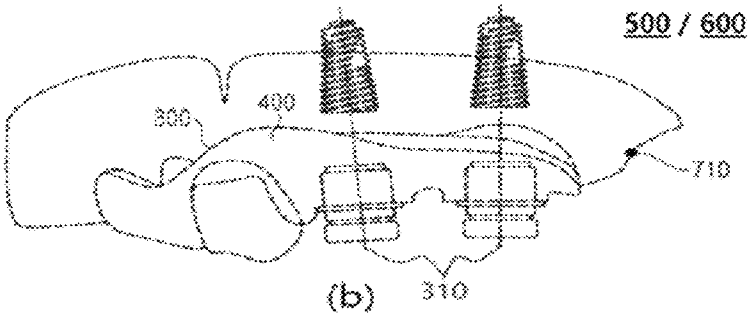
Figure 13:
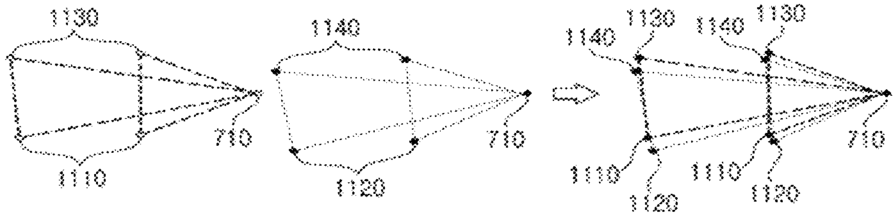
FIG. 13 illustrates an example of a case in which a fit error occurs in the intraoral matching model according to an embodiment.
Figure 13:
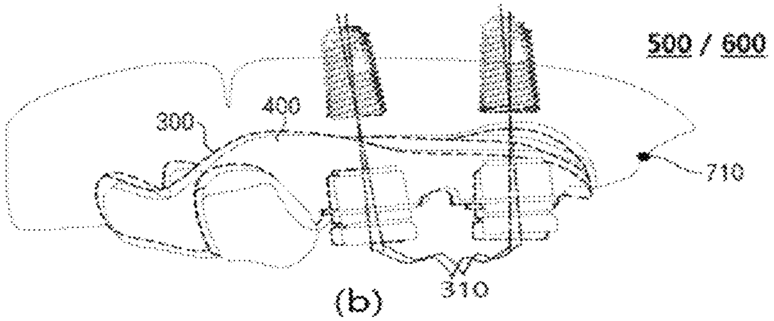

Referring to FIG. 11, as described with reference to FIG. 5, a position at the preset distance 520 away from the fiducial marker plane 820, representing the fastening point between the guide template model 300 and each fiducial marker 410 coupled to the guide template 400, along the implant axis 310 may be determined to be the implant uppermost position 530. The implant uppermost position 530 in the guide wearing simulation model 500 shown on the left in FIG. 11 may indicate a first implant uppermost point 1130 located at the preset distance 520 from the fiducial marker 410 of the guide wearing simulation model 500 along the implant axis 310, and the implant uppermost position 530 in the fiducial marker wearing scan model 600 on the right in FIG. 11 may indicate a second implant uppermost point 1140 located at the preset distance 520 from the fiducial marker 410 of the fiducial marker wearing scan model 600 along the implant axis 310. In addition, the device 100 may determine one of the first reference point 840, the second reference point 850, the third reference point 860, and the fourth reference point 870, which are the plurality of reference points within each fiducial marker 410 in the guide wearing simulation model 500 and the fiducial marker wearing scan model 600, to be a specific reference point. The specific reference point may refer to a point used to obtain expected error information regarding the implant position according to the positional relationship between the uppermost point of each implant and the gingival reference point 710. Referring to FIG. 11, the device 100 may determine one of the plurality of reference points within the fiducial marker 410 of the guide wearing simulation model 500 to be a first specific reference point 1110, and may determine one of the plurality of reference points within the fiducial marker 410 of the fiducial marker wearing scan model 600 to be a second specific reference point 1120. Since the first specific reference point 1110 and the second specific reference point 1120 are the reference points for obtaining the expected error information regarding the implant position according to the position, the positions of the first specific reference point 1110 and the second specific reference point 1120 may be the same positions within each fiducial marker 410. In one embodiment, as shown in FIG. 11, the device 100 may obtain a first figure that includes two triangles, each formed by connecting the first implant uppermost point 1130 located at the preset distance 520 from the fiducial marker plane 820 along the implant axis 310, generated based on the first axial direction, the first specific reference point 1110 in the corresponding fiducial marker 410, and the gingival reference point 710. Also, it may obtain a second figure that includes two triangles, each formed by connecting the second implant uppermost point 1140 located at the preset distance 520 from the fiducial marker plane 820 along the implant axis 310, generated based on the second axial direction, the second specific reference point 1120 in the corresponding fiducial marker 410, and the gingival reference point 710. In one embodiment, the device 100 may match the obtained first and second figures and compare the positions of the reference points. This process may be described with reference to FIGS. 12 and 13. In FIGS. 12 and 13, in order to check the expected error regarding the implant position by matching the guide wearing simulation model 500 and the fiducial marker wearing scan model 600, the first figure corresponding to the guide template model 300 and the guide wearing simulation model 500 may be represented by dotted lines, and the second figure corresponding to the guide template 400 and the fiducial marker wearing scan model 600 may be represented by solid lines.

FIG. 12 illustrates an example of a case in which there is no fit error in an intraoral matching model according to an embodiment.

Referring to (a) shown at the top of FIG. 12, when the first figure and the second figure are matched, it can be seen that the positions of all reference points are the same as shown on the far right in (a), so that the figures are perfectly aligned without error. In addition, referring to (b) shown at the bottom, in the case of an oral fit model, when matched to overlap on the basis of the gingival reference point 710, it can be seen that the guide template model 300 and the guide template 400 are perfectly aligned and thus there is no fit error.

FIG. 13 illustrates an example of a case in which a fit error occurs in the intraoral matching model according to an embodiment.

Referring to (a) shown at the top of FIG. 13, when the first and second figures are matched, it can be seen that the positions of all reference points except the gingival reference point 710 are different, as shown in the upper right illustration. In addition, referring to (b) shown at the bottom, in the case of the oral fit model, it can be seen that when matched to overlap on the basis of the gingival reference point 710, the guide template model 300 and the guide template 400 do not perfectly match and a fit error occurs. Therefore, the device 100 may match the first figure and the second figure formed by connecting the gingival reference point 710 and the specific reference points to compare the positions of each reference point, and may obtain the comparison result of the first expected position and the second expected position for the implant model, thereby obtaining expected error information regarding the implant position. Additionally, the device 100 may additionally provide a graphical UI for providing the guide wearing simulation model 500 and the fiducial marker wearing scan model 600 or the comparison result of the first expected position and the second expected position.

Figure 14:
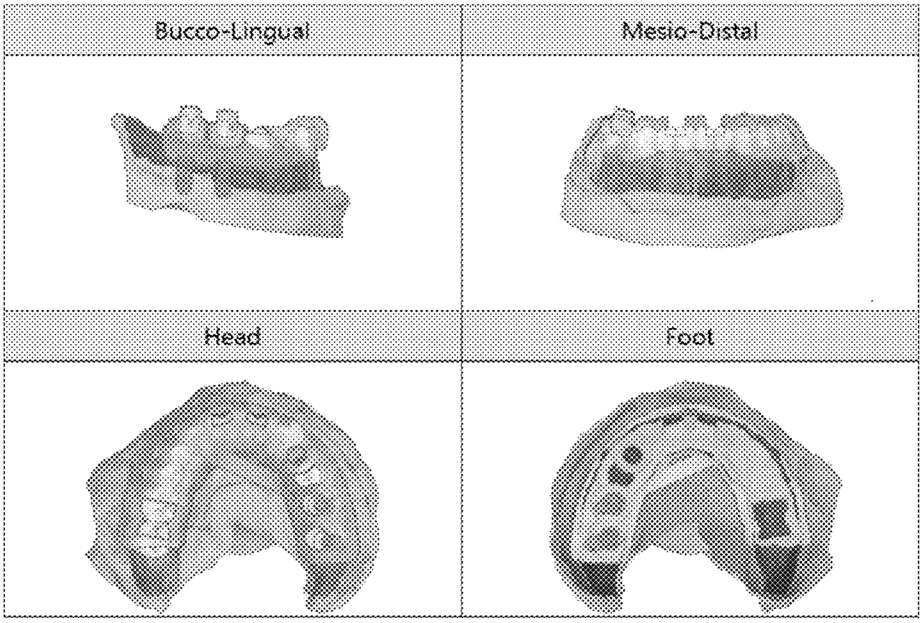
FIG. 14 illustrates an example of a graphical user interface (UI) providing an alignment screen that shows the patient's oral cavity in which a guide template model and a guide template are secured, according to an embodiment.

FIG. 14 illustrates an example of displaying a matching screen that shows the patient's oral cavity in which the guide template model 300 and the guide template 400 are secured, according to an embodiment. As shown in FIG. 14, the device 100 may further visually provide position comparison results between the guide wearing simulation model 500 and the fiducial marker wearing scan model 600, and may match each image of the guide template model 300 and the guide template 400 when worn in the oral cavity to the oral cavity and display the matched image. In FIG. 14, "Bucco-Lingual" represents a buccolingual view and provides an image (side of teeth) as seen from the buccolingual side, and "Mesio-Distal" represents a mesio-occlusal plane and provides an image as seen from the front. In addition, "Head" provides an image as seen from above, and "Foot" provides an image as seen from below, which may be an image obtained by rotating the Head image 180 degrees in the left or right direction. In addition, a rectangular solid at the lower right of each image is a component for identifying the direction of the image. Specifically, it indicates direction information of the current screen that is being displayed in three dimensions, which is displayed as B (Buccal), L (Lingual), A (Anterior), P (Posterior), H (Head), or F (Foot).

Accordingly, the device 100 may provide the user with a visual 3D shape image as an image of the patient's oral cavity in which the guide template model 300 and the guide template 400 are secured.

Figure 15:
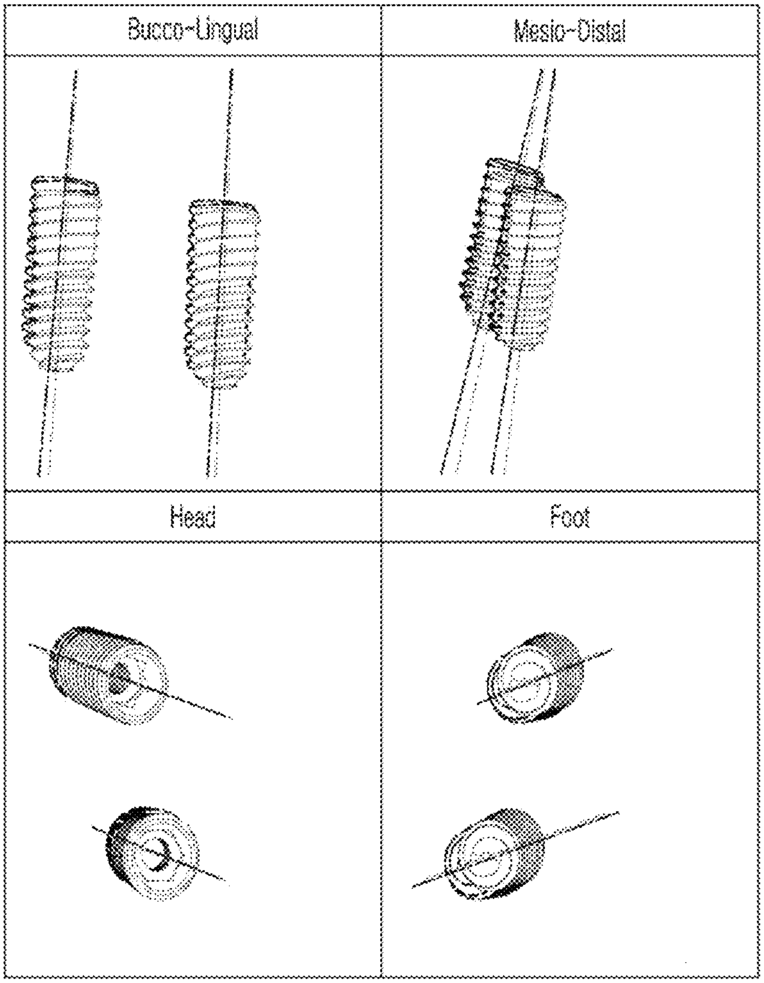
FIG. 15 illustrates an example of a graphical UI providing a screen that shows matched implant images in accordance with the first expected position and the second expected position, according to an embodiment.

FIG. 15 illustrates an example of a graphical UI providing a screen that shows matched implant images in accordance with the first expected position and the second expected position, according to an embodiment. As shown in FIG. 15, the device 100 may further provide a graphical UI for visually providing comparison results of the first expected position and the second expected position for the implant position, and may display and provide an image in which the first expected position and the second expected position for each implant position in the guide template model 300 and the guide template 400 are matched. In FIG. 15, the first expected position is shown in dotted lines and the second expected position is shown in solid lines.

Figure 16:
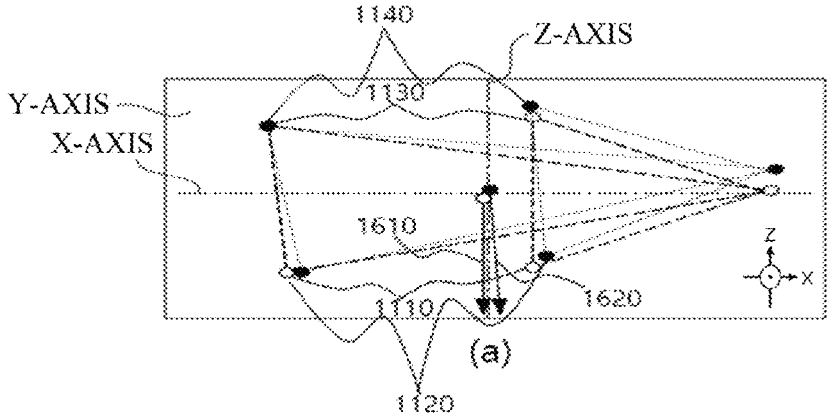
FIG. 16 illustrates an example of a method performed by a device, according to an embodiment, for updating each reference point to eliminate a fit error in the intraoral matching model.
Figure 16:
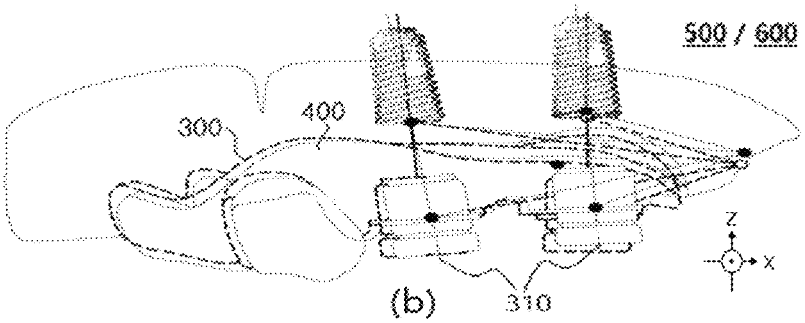

In one embodiment, the device 100 may obtain an intraoral matching model by updating a viewpoint of the first intraoral data or a viewpoint of the second intraoral data in a state where the first gingival reference point and the second gingival reference point are aligned. The viewpoint of the first intraoral data may include the first specific reference point 1110, the first implant uppermost point 1130, and the gingival reference point 710 of the guide wearing simulation model 500, and the viewpoint of the second intraoral data may include the second specific reference point 1120, the second implant top position point 1140, and the gingival reference point 710 of the fiducial marker wearing scan model 600. This may be described with reference to FIG. 16. In FIG. 16, the first figure and guide wearing simulation model 500 are represented by dotted lines, and the second shape and fiducial marker wearing scan model 600 are represented by solid lines.

FIG. 16 illustrates an example of a method performed by a device, according to an embodiment, for updating each reference point to eliminate a fit error in the intraoral matching model.

Referring to FIG. 16, since the first figure and the second figure have the same shapes and sizes, but different positions of each reference point in the vector (X, Y, Z), which causes a fit error, the device 100 may, when a fit error occurs as a result of comparing the first expected position and the second expected position, align the positions of one of the plurality of reference points in the first shape and the second shape, and then rotate or move them with respect to each of the X, Y, Z axes and the origin to ensure matching. Referring to (a) in FIG. 16, the position of the first figure may be updated along a first update direction 1610 corresponding to the guide wearing simulation model 500. In addition, the position of the second figure may be updated along a second update direction 1620 corresponding to the fiducial marker wearing scan model 600. The first update direction 1610 and the second update direction 1620 are illustrated as a downward direction in (a) of FIG. 16, but are not limited thereto, and the update directions may vary depending on the movement direction and angle that make the error rate of the positions of the first figure and the second figure 0 percent. Accordingly, the device 100 may update the positions of the viewpoint of the first intraoral data and the viewpoint of the second intraoral data in the intraoral matching model illustrated in (b) of FIG. 16, thereby allowing the fit error rate of the first figure and the second figure to 0 percent. Accordingly, the device 100 may enhance the accuracy in determining the implant placement position by correcting each viewpoint position by updating when a fit error occurs.

Figure 17:
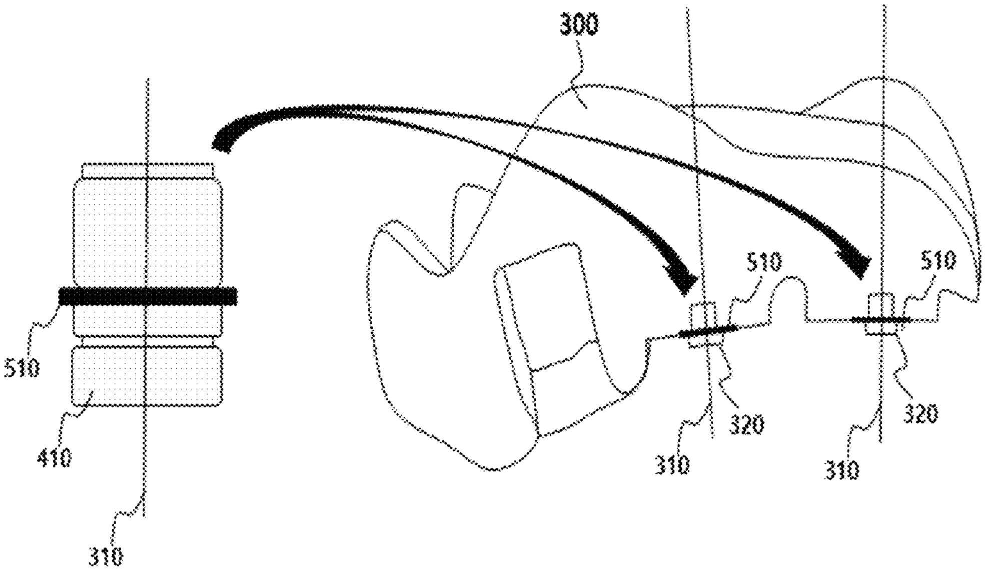
FIG. 17 illustrates an example of a method performed by a device, according to an embodiment, for coupling the fiducial marker to the guide template model.

FIG. 17 illustrates an example of a method performed by the device 100, according to an embodiment, for coupling the fiducial marker 410 to the guide template model 300.

Referring to FIG. 17, the fiducial marker 410 may be coupled to the guide template model 300 such that the implant axis 310 passing through the center of the fiducial marker 410 is aligned with the implant axis 310 located at a position of each drill hole 320 in the guide template model 300 and the widest part 510 of the fiducial marker 410 is aligned with the part shown as 510 in the guide template model 300 in FIG. 17.

According to one embodiment of the present disclosure, the device 100 determines an implant placement position using the fiducial marker 410, and an expected position of a three-dimensional virtual implant is determined only according to a specific shape and position of the fiducial marker 410, which is advantageous and efficient. Also, the device 100 provides expected surgical error information by comparing the position of the three-dimensional virtual implant for which surgery is planned using the fiducial marker 410 with the position of a three-dimensional virtual implant with respect to a position of a guide coupled in a patient's oral cavity, thereby improving efficiency in that the user can utilize the information to correct the coupling of the guide or to redesign a guide.

In addition, the device 100 provides the expected error information regarding the implant placement position to a user account, and correction and production of a guide may be performed according to the information. This allows the implant placement position to be determined at a more appropriate position in the patient's oral cavity, which may improve user and patient satisfaction.

Moreover, because the oral cavity is scanned using an intraoral scanner rather than by having the fiducial marker 410 attached and performing a CT scan, there is no additional radiation exposure.

It should be appreciated that the order and combination of the steps shown above is merely an embodiment of the present disclosure, and the order, combination, branch, function and the performing subject may vary to be implemented with addition, fewer, or different steps without departing from the essential characteristics of each component described in the specification. Throughout this specification, the term "provide (or providing)" may be interpreted as comprehensively including a process in which an object obtains specific information or directly or indirectly transmits or receives specific information to or from a specific object and including the performance of related operations required in this process.

Various embodiments set forth herein may be implemented as software comprising one or more instructions stored in a storage medium (e.g., memory) that is readable by a machine (e.g., a display device or a computer). For example, a processor (e.g., the processor 120) of the machine may invoke at least one of the one or more instructions stored in the storage medium, and execute it. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

It will be understood by those of ordinary skill in the art that various changes in form and details may be made therein without departing from the characteristics described above. The disclosed methods should be considered in a descriptive sense only and not for purposes of limitation. The scope of the present invention is defined not by the detailed description of the present invention but by the appended claims, and encompasses all modifications and equivalents that fall within the scope of the appended claims and will be construed as being included in the present invention.

The invention claimed is:

1. A method performed by a device for providing expected error information related to implant placement, comprising the steps of:

obtaining first intraoral data on the basis of imaging or scanning an oral cavity;

obtaining a guide wearing simulation model for simulating a state in which a guide template model obtained on the basis of the first intraoral data is applied to the intraoral data;

obtaining second intraoral data on the basis of imaging or scanning performed while a guide template corresponding to the guide template model is worn on the oral cavity;

obtaining a fiducial marker wearing scan model indicating a state in which the guide template is worn on the oral cavity on the basis of the second intraoral data; and providing expected error information regarding a position of an implant model by using a first fiducial marker model in which a fiducial marker is coupled to the guide wearing simulation model and a second fiducial marker model corresponding to the fiducial marker wearing scan model.

2. The method of claim 1, wherein the guide template is produced based on the guide template model and is used to couple one or more fiducial markers.

3. T The method of claim 1, wherein the step of providing the expected error information comprises a step of obtaining the expected error information based on a comparison result between a first expected position of the implant model, determined by a position of the first fiducial marker model, and a second expected position of the implant model, determined by a position of the second fiducial marker model.

4. The method of claim 3, wherein the step of providing the expected error information comprises the steps of:

determining the first expected position based on a first axial direction oriented by the first fiducial marker model and positions of a plurality of first reference points on the first fiducial marker;

determining the second expected position based on a second axial direction oriented by the second fiducial marker model and positions of a plurality of second reference points on the second fiducial marker; and obtaining the expected error information based on the comparison result between the first expected position and the second expected position.

5. The method of claim 3, wherein the step of providing the expected error information comprises the steps of:

obtaining a first gingival reference point for the guide wearing simulation model;

obtaining a second gingival reference point for the fiducial marker wearing scan model;

obtaining an intraoral matching model in which the guide wearing simulation model and the fiducial marker wearing scan model are matched with respect to the first gingival reference point and the second gingival reference point corresponding to the first gingival reference point; and superimposing, based on the intraoral matching model, and displaying an implant model of the first expected position and an implant model of the second expected position.

6. The method of claim 1, wherein the step of providing the expected error information comprises the steps of:

automatically or based on user input obtaining a first gingival reference point for the guide wearing simulation model;

obtaining relative position information indicating a relative position relationship between the first gingival reference point and the first fiducial marker model;

obtaining, based on the relative position information, the second gingival reference point, corresponding to the first gingival reference point, on the fiducial marker wearing scan model;

obtaining an intraoral matching model in which the guide wearing simulation model and the fiducial marker wearing scan model are matched by aligning the first gingival reference point and the second gingival reference point; and obtaining the expected error information on the basis of the intraoral matching model.

7. The method of claim 6, wherein a position of the automatically obtained gingival reference point is generated on an area of the entire guide wearing simulation model excluding the guide template model or on an area of the entire fiducial marker wearing scan model excluding the guide template, and the user input is applied to the area of the entire guide wearing simulation model excluding the guide template model or to the area of the entire fiducial marker wearing scan model excluding the guide template model.

8. The method of claim 6, wherein the relative position information includes distance information between a plurality of first reference points on the first fiducial marker model and the first gingival reference point or distance information between a plurality of second reference points on the second fiducial marker model and the second gingival reference point.

9. The method of claim 6, wherein the step of obtaining the intraoral matching model comprises obtaining the intraoral matching model by updating a viewpoint of the first intraoral data or a viewpoint of the second intraoral data in a state where the first gingival reference point and the second gingival reference point are aligned.

10. A device for providing expected error information related to implant placement, the device comprising:

a processor configured to:

obtain first intraoral data on the basis of imaging or scanning an oral cavity;

obtain a guide wearing simulation model for simulating a state in which a guide template model obtained on the basis of the first intraoral data is applied to the intraoral data;

obtain second intraoral data on the basis of imaging or scanning performed while a guide template corresponding to the guide template model is worn on the oral cavity;

obtain a fiducial marker wearing scan model indicating a state in which the guide template is worn on the oral cavity on the basis of the second intraoral data; and provide expected error information regarding a position of an implant model by using a first fiducial marker model coupled to the guide wearing simulation model and a second fiducial marker model coupled to the fiducial marker wearing scan model.

11. The device of claim 10, wherein the guide template is produced based on the guide template model and is used to couple one or more fiducial markers.

12. The device of claim 10, wherein the processor is configured to obtain the expected error information based on a comparison result between a first expected position of the implant model, determined by a position of the first fiducial marker model, and a second expected position of the implant model, determined by a position of the second fiducial marker model.

13. The device of claim 12, wherein the processor is configured to determine the first expected position based on a first axial direction oriented by the first fiducial marker model and positions of a plurality of first reference points on the first fiducial marker, determine the second expected position based on a second axial direction oriented by the second fiducial marker model and positions of a plurality of second reference points on the second fiducial marker, and obtain the expected error information based on the comparison result between the first expected position and the second expected position.

14. The device of claim 10, wherein the processor is configured to automatically or based on user input obtain a first gingival reference point for the guide wearing simulation model, obtain relative position information indicating a relative position relationship between the first gingival reference point and the first fiducial marker model, obtain, based on the relative position information, the second gingival reference point, corresponding to the first gingival reference point, on the fiducial marker wearing scan model, obtain an intraoral matching model in which the guide wearing simulation model and the fiducial marker wearing scan model are matched by aligning the first gingival reference point and the second gingival reference point, and obtain the expected error information on the basis of the intraoral matching model.

15. A computer-readable, non-transitory recording medium having stored thereon a program which, when executed by a computer system, causes the computer system to implement a method for providing expected error information related to implant placement, wherein the method comprises the steps of:

obtaining first intraoral data on the basis of imaging or scanning an oral cavity;

obtaining a guide wearing simulation model for simulating a state in which a guide template model obtained on the basis of the first intraoral data is applied to the intraoral data;

obtaining second intraoral data on the basis of imaging or scanning performed while a guide template corresponding to the guide template model is worn on the oral cavity;

obtaining a fiducial marker wearing scan model indicating a state in which the guide template is worn on the oral cavity on the basis of the second intraoral data; and providing expected error information regarding a position of an implant model by using a first fiducial marker model in which a fiducial marker is coupled to the guide wearing simulation model and a second fiducial marker model corresponding to the fiducial marker wearing scan model.

16. The computer-readable, non-transitory recording medium of claim 15, wherein the step of providing the expected error information comprises a step of obtaining the expected error information based on a comparison result between a first expected position of the implant model, determined by a position of the first fiducial marker model, and a second expected position of the implant model, determined by a position of the second fiducial marker model.

17. The computer-readable, non-transitory recording medium of claim 16, wherein the step of providing the expected error information comprises the steps of:

determining the first expected position based on a first axial direction oriented by the first fiducial marker model and positions of a plurality of first reference points on the first fiducial marker;

determining the second expected position based on a second axial direction oriented by the second fiducial marker model and positions of a plurality of second reference points on the second fiducial marker; and obtaining the expected error information based on the comparison result between the first expected position and the second expected position.

18. The computer-readable, non-transitory recording medium of claim 16, wherein the step of providing the expected error information comprises the steps of:

obtaining a first gingival reference point for the guide wearing simulation model;

obtaining a second gingival reference point for the fiducial marker wearing scan model;

obtaining an intraoral matching model in which the guide wearing simulation model and the fiducial marker wearing scan model are matched with respect to the first gingival reference point and the second gingival reference point corresponding to the first gingival reference point; and superimposing, based on the intraoral matching model, and displaying an implant model of the first expected position and an implant model of the second expected position.

19. The computer-readable, non-transitory recording medium of claim 15, wherein the step of providing the expected error information comprises the steps of:

automatically or based on user input obtaining a first gingival reference point for the guide wearing simulation model;

obtaining relative position information indicating a relative position relationship between the first gingival reference point and the first fiducial marker model;

obtaining, based on the relative position information, the second gingival reference point, corresponding to the first gingival reference point, on the fiducial marker wearing scan model;

obtaining an intraoral matching model in which the guide wearing simulation model and the fiducial marker wearing scan model are matched by aligning the first gingival reference point and the second gingival reference point; and obtaining the expected error information on the basis of the intraoral matching model.

20. The computer-readable, non-transitory recording medium of claim 19, wherein the step of obtaining the intraoral matching model comprises obtaining the intraoral matching model by updating a viewpoint of the first intraoral data or a viewpoint of the second intraoral data in a state where the first gingival reference point and the second gingival reference point are aligned.

* * * * *